United States Patent [19]

Range et al.

[11] Patent Number: 4,839,391

[45] Date of Patent: Jun. 13, 1989

[54] METHOD AND REACTOR FOR CATALYTIC METHANIZATION OF A GAS CONTAINING CO, $CO_2$ AND $H_2$

[75] Inventors: Jochen Range, Jülich; Bernd Höhlein, Linnich-Tetz; Hans Niessen, Düren; Volker Vau, Jülich-Broich; H. J. R. Schiebahn, Niederzier; Horst Hoffmann, Alsdorf; Manfred Vorwerk, Erkelenz, all of Fed. Rep. of Germany

[73] Assignees: Kernforschungsanlage Julich GmbH, Julich; Rheinische Braunkohlenwerke AG, Cologne, both of Fed. Rep. of Germany

[21] Appl. No.: 207,024

[22] Filed: Jun. 13, 1988

Related U.S. Application Data

[63] Continuation of Ser. No. 39,604, Apr. 16, 1987, abandoned.

[30] Foreign Application Priority Data

Apr. 16, 1986 [DE] Fed. Rep. of Germany ....... 3612734

[51] Int. Cl.$^4$ .............................................. C07C 1/02
[52] U.S. Cl. ............................................... 518/712
[58] Field of Search .................................... 518/712

[56] References Cited

U.S. PATENT DOCUMENTS 2,662,911 12/1953 Dorschner et al. ................ 518/712
4,258,006 3/1981 Flockenhaus et al. ............. 518/712

OTHER PUBLICATIONS

Welty et al, Fundamentals of Momentum, Heat and Mass Transfer, 2nd Ed., John Wiley & Sons, N.Y., (1976), pp. 408–409.

*Primary Examiner*—Howard T. Mars
*Attorney, Agent, or Firm*—Frishauf, Holtz, Goodman & Woodward

[57] ABSTRACT

A single stage methanization reactor and process are made to yield a product gas of high methane content as well as useful superheated steam without overheating the catalyst bed in which a synthesis gas containing, CO, $CO_2$ and $H_2$ is converted into product gas. A variety of dispositions of vaporizer and superheater portions of the cooling system in the catalyst bed, for which the temperature profiles of gas and coolant along the reactor length are shown and compared, illustrate the principles governing the cooling system for such a reactor. A small portion of the superheated steam is mixed with preheated synthesis gas for elimination of all or part of the carbon monoxide content before the synthesis gas is introduced into the methanization reactor.

6 Claims, 5 Drawing Sheets

METHOD AND REACTOR FOR CATALYTIC METHANIZATION OF A GAS CONTAINING CO, $CO_2$ AND $H_2$

This application is a continuation of application Ser. No. 039,604, filed Apr. 16, 1987, now abandoned.

This invention concerns a method and reactor for methanization of a synthesis gas contaning carbon monoxide, carbon dioxide and hydrogen. The methanization takes place in a bed of solid catalyst which is cooled by a cooling medium. In the catalyst bed the synthesis gas flows successively through an inflow region for the synthesis gas, then through a region of higher synthesis gas temperature that is referred to hereinafter as a hot spot region and, finally, through an outward gas-flow region in which the synthesis gas temperatures drop off consistently. The cooling medium which carries away the heat generated in the bed of solid catalyst serves for the generation of vapor and is converted into superheated vapor.

The conversion of a synthesis gas containing carbon monoxide, carbon dioxide and hydrogen, since it runs exothermally, is useful for the recovery of energy. It is known to carry out the conversion of the synthesis gases in internally cooled reactors containing catalysts. The internally cooled reactors have cooling systems through which the cooling medium flows for vapor generation which are disposed with the catalyst bed. The cooling is operated with care to assure that the maximum pemissible operating temperature for the catalyst is not exceeded, so that the catalyst material remains stable.

Internally cooled reactors for methanization of synthesis gas were described in an article by B. Höhlein, "Methanisierungsverfahren unter Berücksichtigung der Arbeiten zum NFE-Projekt", Berichte der Kernforschungsanlage Jülich, JÜL-1589, May 1979. The installations shown in this publication, especially FIG. 10, make possible the carrying out of the process without recirculation of gas by means of failure-prone compressors.

It is known from DE-OS No. 29 49 588 to connect two or more reactors one behind the other for the generation of superheated saturated steam in which case one of the reactors, the one through which the synthesis gas first flows, is constituted as an adiabatic reactor and the following reactor as an internally cooled reactor. The heat arising in the internally cooled reactor is removed by vaporization of the cooling medium. The superheating of the cooling medium takes place in heat exchange with the synthesis gas flowing out of the adiabatic reactor.

The methanization process known from German Patent No. 31 21 991 shows no difference from the process just mentioned with regard to the steam or vapor generation in the internally cooled reactor and the superheating of the steam with synthesis gas which is leaving the adiabatic reactor. Of the three reactors through which the synthesis gas passes in succession in these known processes, the first is for the generation of vapor at the vaporization temperature, the second reactor operates adiabatically, and the third reactor is used for heating the cooling medium up to the vaporization temperature. The synthesis gas flowing away from the adiabatic reactor serves for superheating the vaporized cooling medium.

Apart from the apparatus expense involved in the provision of several reactors to be passed through one after the other and the arrangement of supplementary heat exchangers for superheating the generated vapor, the known processes also have disadvantages regarding the control and carrying out of the process. It is necessary, in order to prevent overheating the catalyst, to provide intermediate cooling of the synthesis gas between the individual reactors, so that the methanization process as a whole can be carried out only stepwise.

SUMMARY OF THE INVENTION

It is an object of the invention to provide a one-stage process for the methanization of synthesis gas which makes possible both the generation of superheated coolant vapor and also the generation of a methane-rich product gas, while furthermore, making it possible to maintain within the catalyst bed, even in the hot spot region, a sufficient operating temperature which does not impair the stability of the catalyst.

Briefly, the cooling medium is made to vaporize at its boiling temperature at least in the outward gas-flow region of the catalyst bed, and the vapor thereby formed is superheated in the hot spot region of the catalyst bed. By this process management of an extensively constant temperature of the cooling medium in the gas outflow region of the catalyst bed, and likewise the superheating of the generated vapor in the hot spot region can be provided in a simple way in the optimal active region of the catalyst bed.

A lower maximum temperature in the hot spot region results when the hot spot region is used for some of the vaporization of the cooling medium. In this case the reaction heat produced in the hot spot region serves not only for producing superheated vapor, but a part of the heat is also absorbed for vaporization of the cooling medium, a feature that facilitates the controllability of the desired course of the process.

The reactor may be provided with particular features capable of contributing to the efficiency and controllability of the process which will be better understood in the context of a detailed description.

BRIEF DESCRIPTION OF THE DRAWINGS

The process and reactor of the invention are further described by way of illustrative example with reference to the annexed drawings, in which.

Figure 2:
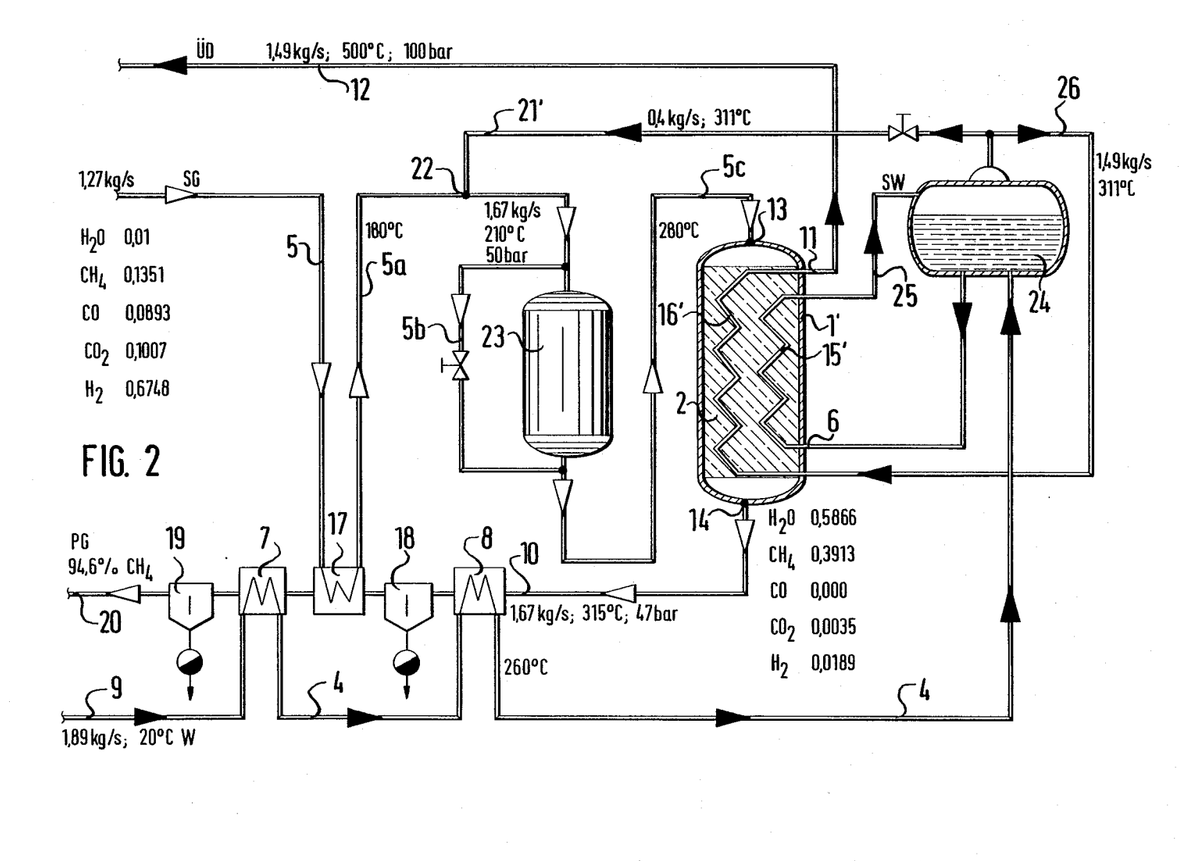
FIG. 2 is a process flow diagram for a methanization apparatus similar to FIG. 1, but having a vapor chamber between the vaporizer and the super heater.

The following abbreviations are used in the drawings to designate the flow of reaction gas and of cooling $H_2O$:

SG: synthesis gas
W: cooling water
ÜD: superheated steam
PG: product gas
SW: boiling water
SD: saturated steam The product gas is the methane-rich gas produced by the process by treatment of synthesis gas. Typical composition of gases is shown in FIG. 2, as well as temperatures and pressures. In the illustrated embodiments water is used as the cooling medium.

DESCRIPTION OF THE ILLUSTRATED EMBODIMENTS

Figure 1:
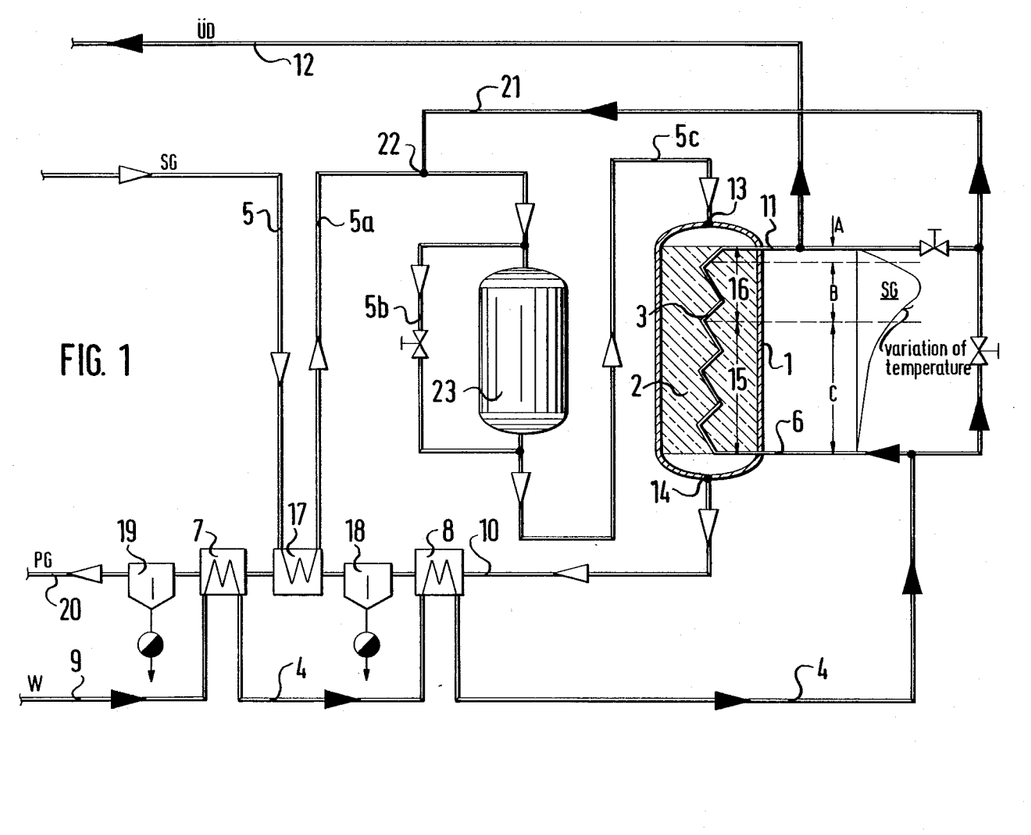
FIG. 1 is a process flow diagram of a single stage methanization reactor installation.

FIG. 1 shows a methanization installation comprising a methanization reactor 1 which contains a catalyst bed 2 through which a cooling system 3 passes. The cooling medium flows through the cooling system 3 in countercurrent to the flow of synthesis gas through the bed. The direction of flow of the coolant in the coolant line 4 is shown in each case by solid, dark arrowheads in the drawing, while the direction of flow of the synthesis gas in the synthesis gas line 5 is illustrated with light arrowheads (open triangles).

Water serves as the coolant and is passed first through preheaters 7 and 8 before entering the methanization reactor at its coolant inlet 6. The cooling water comes into the system at room temperature through the supply line 9 and, in the preheaters 7 and 8, it is heated by the product gas from the methanization reactor that flows away through the line 10 to the preheater 8 and later away from the system as a whole through the output line 20. The water is thus preheated to the necessary input temperature for it at the coolant inlet 6 of the reactor. The water is then vaporized and thereafter superheated by absorption of the heat arising in the catalyst bed 2 from the methanization of the synthesis gas. The superheated steam flows out of the methanization reactor from the coolant outlet 11 into a steam line 12.

As seen in the direction of flow of the synthesis gas, the methanization reactor 1 has three successive zones of characteristic temperature distribution in the catalyst bed 2. Corresponding to this temperature profile in the catalyst bed, the methanization reactor when operated in a stable operation mode can be subdivided into a gas inflow region A with steeply rising temperature, a hot spot region B having a temperature maximum in the catalyst bed and an outward gas flow region C with steadily falling temperature. These three zones and their characteristic temperature profile, as seen in the direction of flow of the synthesis gas, are schematically shown for the length of the catalyst bed in FIG. 1 by a shaded curve diagram at the right of the reactor. The gas inflow region A is characterized by rising synthesis gas temperatures from about 250° C. up to about 450° C., the hot spot region by synthesis gas temperatures between 450° C. and 750° C. and the outward gas flow region by declining temperatures from about 450° C. to about 250° C. In the illustrated embodiment of FIG. 1, the cooling system 3 traverses, in the direction of flow of the coolant, not only the outward gas flow region C and the hot spot region B, but also the gas inflow region A of the reactor. The synthesis gas flows in the methanization reactor in countercurrent to the coolant. It is introduced into the methanization reactor at the synthesis gas inlet 13 and is immediately strongly heated by the onset of the exothermic methanization reaction in the catalyst bed 2. In the hot spot region B, the synthesis gas reaches its maximum temperature. It is converted into product gas and after cooling and further conversion in the outward gas flow region C, it leaves the methanization reactor as a methane-rich product gas. The product gas flows out of the methanization reactor from the product gas outlet 14 and away into the product gas line 10.

For cooling of the outward gas flow region C of the methanization reactor, the heat which is present there is carried out of the catalyst bed by vaporization of the coolant in the cooling system 3. In the hot spot region B, the heat there arising is drawn away from the catalyst bed by super-heating of the steam that is formed. The cooling system 3 thus operates in the outward gas flow region C as a vaporizer 15 for the coolant and in the hot spot region B as a superheater 16 for the coolant vapor produced in the vaporizer.

In the methanization reactor shown in FIG. 1, the vaporizer 15 and the superheater 16 merge into one another at or near the boundary between the hot spot region and the region of outward gas flow. There is thus no fixed limit in the cooling system 3 between a vaporizer 15 and superheater 16. It is important, however, that within the part of the cooling system 3 that operates as a superheater, the heat produced in the hot spot region B should be removed and should serve to superheat the vapor (steam) produced in the vaporizer 15 of the cooling system 3. The temperature of the coolant thereby rises in the superheater 16. In the cooling system of the embodiment shown in FIG. 1, which passes through the inflow region 13 of the bed 2 as well as through the rest of the bed 2, the temperature of the coolant merely falls off slightly in this region towards the coolant outlet 11. In the vaporizer 15, however, the coolant is at a constant temperature, namely the boiling temperature for the pressure level. From this difference, the vaporizer or boiler 15 and the superheater 16 can be distinguished from each other in the cooling system 3 of FIG. 1 by the distribution of temperature of the coolant over these respective portions of the system.

The product gas flowing out of the outlet 14 is led in the product gas line 10 to the preheaters 7 and 8 and there exchanges a part of its heat, as already mentioned, with the coolant flowing into the methanization plant. In addition to these preheaters 7 and 8, there is also a preheater 17 in the product gas line 10 for preheating the synthesis gas which flows into the methanization plant. Liquid separators 18 and 19 are also interposed in the product gas output line 10 for separating water out of the the product gas. The dry methane-rich product gas leaves the methanization plant at the gas outlet 20.

The superheated steam formed in the methanization reactor 1 is removed by the steam line 12 in the illustrative emoodiment of FIG. 1, as a work producing medium, for example to be supplied to steam turbines for generating electrical energy. In part, however, the superheated steam, by control of the valves 21a and 21b can be mixed with preheated cooling water from the line 21' branching off the line 4 to produce saturated steam delivered by the steam line 21 into the synthesis gas 5. It could be put into the line 5 where the synthesis gas has yet to flow into the preheater 17, but in the illustrated example it is shown connected at 22 into the part 5a of the synthesis gas line 5 that follows the preheater 17. After the mixing in of steam, the synthesis gas can be supplied entirely or in part into a conversion reactor 23 in order to convert the carbon monoxide contained in the synthesis gas partly into carbon dioxide. The portion of synthesis gas that is not so converted flows through a regulatable bypass 5b connected in parallel to the conversion reactor 23 and then proceeds along with the converted part of the synthesis gas into the methanization reactor 1.

The methanization reactor 1' shown in FIG. 2 differs from the reactor of FIG. 1 by having a vaporizer 15' and a superheater 16' which form tube systems in the catalyst bed of the reactor which are separated from each other. A steam chamber 24 is interposed between the vaporizer 15' and the superheater 16'. The steam flowing in from the vaporizer 15' through a connecting line 25 collects in the steam chamber 24 where still unvaporized cooling water carried along with the steam is separated. At the highest place of the steam chamber 24, a steam line 26 is connected to lead the collected dry steam to the superheater 16'. Just as in FIG. 1, the line 21' for drawing off steam to the connection 22, is provided, being branched off in this case from the steam line 26 leading out of the steam chamber 24 and, again, leads into the portion 5a of the synthesis gas line 5. Here again, therefore, as in FIG. 1, saturated steam is introduced into the synthesis gas.

In the illustrated example, the steam chamber 24 is located outside the methanization reactor 1. That is not necessary, however, and it is also possible to locate the steam chamber inside the methanization reactor as an integrated component thereof. The steam chamber in such a case can conveniently be located above the catalyst bed and the synthesis gas entering into the methanization reactor can be led to flow around and along the walls of the steam chamber.

In FIGS. 1 and 2 the vaporizers 15, 15' and superheaters 16, 16' are only schematically shown. They can also be placed in the catalyst bed in other ways than those shown in FIGS. 1 and 2. In all cases, however, there is a vaporizer in the outward gas flow region C of the methanization reactor and a superheater in the hot spot region B. Particular kinds of embodiments for the arrangement of vaporizer and superheater are shown in FIGS. 3 to 8. These figures also show the temperature profiles which establish themselves in the confines of the catalyst bed 2 both in the synthesis gas and in the coolant.

Figure 6:
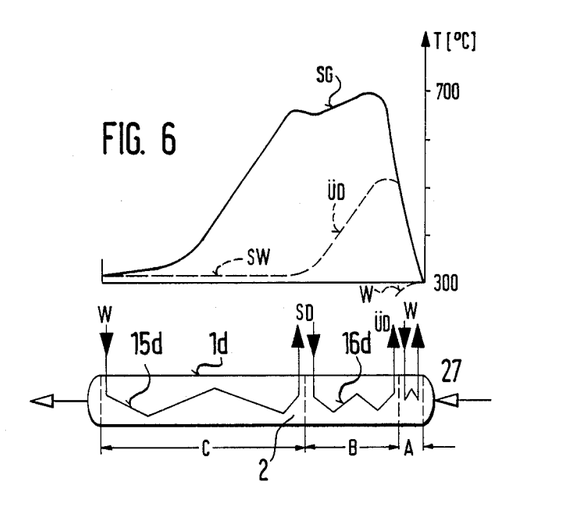
FIG. 6 is a graph with scale diagram of the same kind as FIGS. 3, 4 and 5 for a case like FIG. 5, except that there is supplementary cooling in the gas inflow region of the bed (the gas inflow region serving for coolant modification)
Figure 7:
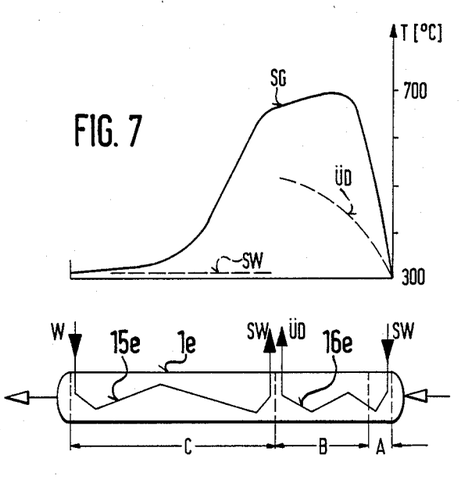
FIG. 7 is a graph with scale diagram similar to the preceding figures for the case of a catalyst bed having a separate vaporizer and superheater of its cooling system in which the vaporizer for the vapor to be superheated provides flow of the coolant in the same direction as the gas flow.

The temperatures are shown both for the synthesis gas and for the coolant over the reactor length in the respective directions of flow of the synthesis gas and of the coolant. The temperature profile for the synthesis gas over the reactor length is shown in solid lines in the figures, while the temperature profile for the coolant is given in broken lines. In all illustrative embodiments, the synthesis gas flows through the methanization reactor 1 from the synthesis gas input 13 to the product gas outlet 14. The direction of flow of the coolant in the vaporizer is always opposite to the direction of flow of the synthesis gas. In the superheater it is also possible, however, to lead the coolant vapor in the same direction as the flow of synthesis gas, as is shown in the embodiment of FIG. 7. The respective directions of flow are shown in FIG. 3–8 in the same way as in FIGS. 1 and 2 with dark flow arrowheads for the coolant and open triangle arrowheads for the synthesis gas.

Figure 3:
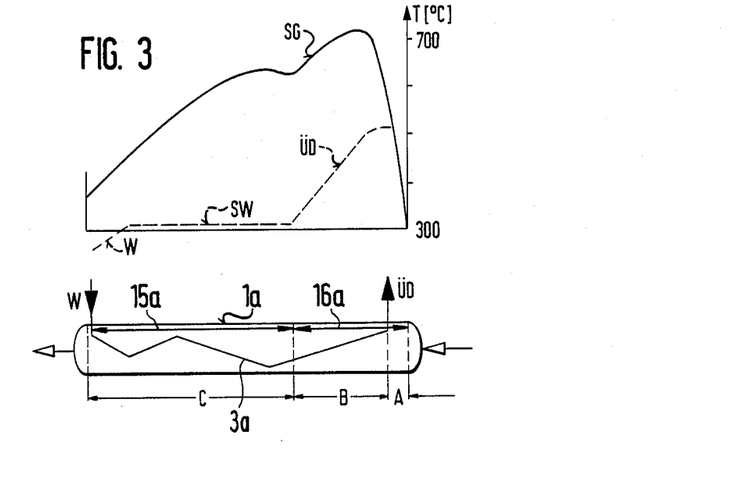
FIG. 3 is a graph of the temperature in a water-cooled bed of a methanization reactor with counter-current flow of the cooling medium and the synthesis gas without flow of coolant through the gas inflow zone of the bed, with a reactor diagram drawn next to the horizontal axis of the graph for serving as a scale.

FIG. 3 shows a methanization reactor 1a in which the catalyst bed 2 has a cooling system 3a passing both through its outward gas flow region C and its hot spot region B. In the outward gas flow region C, the cooling system 3a serves as a vaporizer 15a and in the hot spot region B it serves as superheater 16a. The cooling water flows into the vaporizer 15a at a temperature below the boiling point, is then brought to the vaporization (boiling) temperature in the vaporizer 15a, is vaporized and then, in the superheater 16a, it is superheated. The regenerated reaction heat is taken up by cooling water in the gas outflow region C and by steam in the hot spot region B. In the latter region, the steam is heated up to a temperature of about 500° C. at 100 bar, while the catalyst bed 2 in that region remains below the adiabatic temperature which, for the synthesis gas used in the illustrated embodiment, lies below 800° C. At the transition from the hot spot region B to the outward gas flow region C, as the result of the heat taken up at constant boiling temperature by the vaporizer 15a, a local discontinuity or "kink" appears in the temperature profile which is mainly related to the reactor construction, especially in an embodiment of the methanization reactor of the kind described in German Published Patent Application DE-OS No. 32 47 821. The temperature there, oddly enough, increases slightly before resuming its decline which thereafter continues down to values under 400° C.

Figure 4:
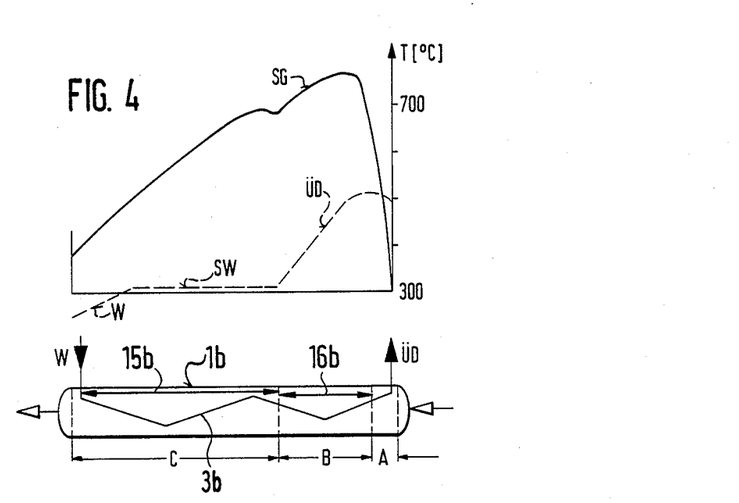
FIG. 4 is a graph with horizontal scale diagram as in FIG. 3, illustrating the temperature in the reactor in which the cooling system includes both the gas inflow zone and the gas outflow zone.

The methanization reactor 1b shown in FIG. 4 has a cooling system 3b that passes through the entire methanization reactor, including its output gas flow region C, hot spot region B and gas inflow region A. The cooling system 3b with its vaporizer portion 15b and its superheater portion 16b thus corresponds to the cooling system 3 illustrated in FIG. 1. The corresponding temperature profiles in FIG. 4 show temperature characteristics that are in principle comparable to those of the methanization reactor according to FIG. 3. The superheated steam is cooled down somewhat below its maximum temperature of 500° C. in the gas inflow region A, however, by the inflowing synthesis gas. The notable difference in comparison to the embodiment of FIG. 3, however, is the strong increase of the maximum temperature of the synthesis gas in the hot spot region. The synthesis gas is heated in the catalyst bed 2 in this case up to a temperature of about 770° C. The exit temperature of the product gas is consequently also raised slightly compared to the exit temperature of the product gas in the embodiment of FIG. 3, but nevertheless still lies below 400° C.

Figure 5:
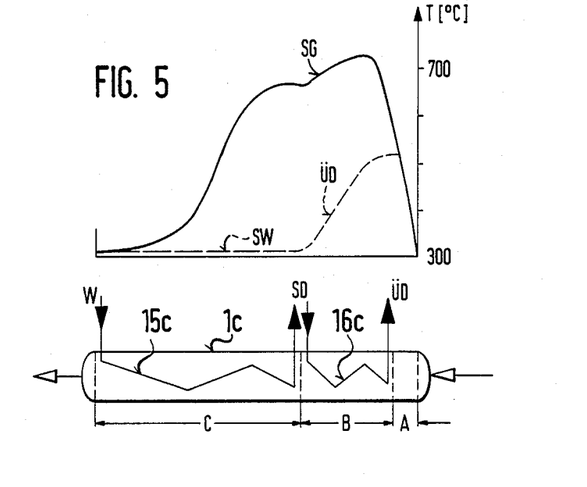
FIG. 5 is a graph and scale diagram of the same kind as FIGS. 3 and 4 for the case of a catalyst bed in which the vaporizer part of the coolant circulation is separate from the superheater part of the coolant circulation, without coolant circulation in the gas inflow zone of the bed, coolant circulation again being countercurrent to gas flow.

In the embodiment illustrated in FIG. 5, the methanization reactor 1c has mutually separated piping systems for the vaporizer 15c and the superheater 16c. The vaporizer 15c is located exclusively in the outward gas flow region C of the methanization reactor and the hot spot region B is cooled only by superheating steam. In this and the following examples of embodiments, the coolant enters the vaporizer 15c already at the vaporization (boiling) temperature. In the embodiment of FIG. 5, the temperatures established in the hot spot B region are about the same temperatures that appear in the corresponding part of the embodiment of FIG. 3. The synthesis gas is heated to a maximum of about 730° C. in the methanization reactor. A stronger cooling down of the product gas is obtained, however. The product gas passes out of the reactor at a temperature of about 310° C. The methanization reactor 1d shown in FIG. 6 is equipped in the same way as the methanization reactor 1c of FIG. 5 so far as concerns the vaporizer 15d and the superheater 16d. In addition, however, it has a coolant preheater 27 in the gas inflow region A, also with separate piping. In that preheater 27 the coolant is brought up to the boiling temperature before its entry into the vaporizer 15d and only thereafter is brought as directly as possible to the coolant inlet 6 of the vaporizer 15d. The coolant is made to flow in its preheater 27 in countercurrent to the synthesis gas. By this cooling of the synthesis gas provided in the gas inflow region A, the maximum heating of the catalyst bed in the methanization reactor 1d is limited to about 700° C.

A maximum temperature of 700° C. in the hot spot region B can also be obtained with the embodiment illustrated in FIG. 7. In this case, the steam to be superheated in the superheater 16e is caused to flow in a manner concurrent with the synthesis gas flow. The superheater 16e is located so that it is both in the hot spot region B and in the gas inflow region A of the methanization reactor 1e. The steam to be superheated is supplied at the boiling temperature to the gas inflow region A. In this methanization reactor, also, the steam is heated up to a temperature of about 500° C. The product gas flows out of the methanization reactor at a temperature of about 310° C.

Figure 8:
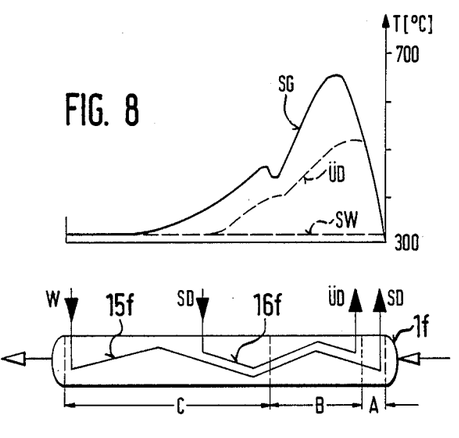
FIG. 8 is a graph with scale diagram similar to the preceding figures showing the temperature in the catalyst bed with a cooling system which provides vaporization if the cooling medium in the hot spot zone as well as in the gas inflow region of the methanization reactor.

Very great lowering of the temperature maximum in the hot spot region B is obtained by the construction of the cooling system in accordance with FIG. 8. In this embodiment, the vaporizer 15f of the cooling system stretches over the entire length of the catalyst bed including the outward gas flow region C, the hot spot region B and the gas inflow region A of the methanization reactor 1f. The superheater 16f is disposed in the hot spot region B but it projects also into the outward gas flow region C of the methanization reactor, so that the superheater 16f and vaporizer 15f overlap for the full length of the superheater 16f. In this case, the necessary heat transfer simultaneously to the superheater 16f and to the vaporizer 15f can be obtained in a convenient construction design by running the steam superheating piping within catalyst tubes containing the catalyst particles, so that the reaction heat can be passed over both to the coolant that is to be vaporized which surrounds the catalyst tubes and also to the vapor that is to be superheated. In this embodiment the maximum temperature of the synthesis gas can be reduced down to 650° C. without deterioration of the quality of the working medium produced, namely the steam superheated up to 500° C. at 100 bars, and without reduction of the methane content in the product gas. Methanization reactors of this kind are therefore optimally suited for carrying out the methanization reaction.

OPERATION EXAMPLE

FIG. 8 will be recognized as illustrating in more detail a reactor of the kind represented more generally in FIG. 2. There are according tabulated in FIG. 2 flow rates, gas compositions, temperatures and pressures for the operation of a system such as is shown in FIG. 2 with a reactor equipped for cooling in the manner shown in FIG. 8. In the illustrated case, the synthesis gas is introduced into the methanization plant at a rate of 1.27 kg/s, the gas having the following composition in % by volume: 1% $H_2O$; 13.51% $CH_4$; 8.93% CO; 10.07% $CO_2$, and 67.48% $H_2$. The synthesis gas is heated up to about 180° C. in the preheater 17 and is then mixed with saturated steam in the portion 5a of the synthesis gas line 5. With the bypass 5b closed, all of the synthesis gas is converted at a temperature of 210° C. and a pressure of 50 bars in the converter 23. The synthesis gas is thereby further heated and then flows at a temperature of 280° C. to the synthesis gas input 13 into the methanization reactor 1'.

After methanization of the synthesis gas, in the methanization reactor, there is obtained at the product gas outlet 14 a gas of the composition, again in % by volume, of 58.66% $H_2O$; 39.13% $CH_4$; 0% CO; 0.35% $CO_2$ and 1.89% $H_2$. This product gas flows out of the methanization reactor at a pressure of 47 bars and a temperature of 350° C. The mass rate of flow of the product gas in the product gas line amounts of 1.67 kg/s. After flowing through the preheaters 8, 17 and 7, and after separation of water in the liquid separators 18 and 19, a product gas is obtained at the gas outlet 20 having a volumetric $CH_4$ content of 94.6%. In order to remove the heat produced in the methanization plant, cooling water is supplied at a temperature of about 20° C. into the cooling feedline 9 at the rate of 1.89 kg/s. The cooling water is heated up to a temperature of 260° C. in passing through the preheaters 7 and 8, at which temperature it is introduced into the steam chamber 24 in the illustrated case. In the steam chamber, the cooling water is brought up to a temperature of 310° C. at a pressure of 100 bars and then it is introduced into the vaporizer (boiler) 15', in which it is converted to steam at a vaporization temperature of 311° C. The steam produced is led back into the steam chamber 24 and then flows over the connecting line 25 into the superheater 16'. The steam is superheated here to 500° C. at 100 bars. Superheated steam is led away out of the methanization plant at the rate of 1.49 kg/s. The remainder of the steam flows from the steam chamber 24 at the rate of 0.4 kg/s over the draw-off line 21' and into the synthesis gas at the connection 22.

The data tabulated in FIG. 2 for the synthesis gas and the cooling water hold with little variation also for the methanization plant illustrated in FIG. 1. They apply also for data external to the methanization reactor for the embodiments of FIG. 3–7. Account needs to be taken merely of the different temperatures for the embodiments illustrated in FIGS. 3 and 4 and also of the superheated steam outflow temperature below 500° C. which distinguishes the embodiment of FIG. 4 from all the others. The temperature profiles shown in FIGS. 3–7 are semiquantitative: they are quantitative with respect to the vertical scale.

Although the invention has been described with respect to a number of illustrative examples, it will be recognized that further variations and modifications are possible within the inventive concept.

We claim:

1. Process for catalytic methanization of a synthesis gas containing carbon monoxide, carbon dioxide and hydrogen in a reactor containing a bed of solid catalyst which is cooled by cooling water, wherein said synthesis gas flows, in passing through said catalyst bed, successively through an inflow region for the synthesis gas, a hot spot region and an outward gas flow region of temperature substantially declining along an outward gas flow path therein, said cooling water being converted into steam by the transfer of heat arising from methanization and said steam being superheated in said hot spot region, and wherein:

said cooling water flows, in countercurrent to said synthesis gas flowing through said catalyst bed, in a cooling water path includes one complete transit through said catalyst bed, and the conversion of water from its liquid state into steam is produced by heat transfer both in said outward gas flow region and in said hot spot region.

2. Process according to claim 1, wherein said water is passed through said outward gas flow region, said hot spot region and said gas inflow region in a first countercurrent pass (15', 15f) through said reactor for vaporization into steam and is thereafter passed through a portion of said gas outflow region adjoining said hot spot region and then through said hot spot region in a second countercurrent pass (16', 16f) for superheating of steam produced in said first pass (15', 15f).

3. Process according to claim 2, wherein after said first pass (15') of cooling water through said reactor for vaporization into steam, the steam thereby produced is delivered to a steam chamber (24) from which steam is led away for the step of passing it, in said second countercurrent pass (16'), for superheating thereof.

4. Process for catalytic methanization of a synthesis gas containing carbon monoxide and hydrogen in a reactor containing a bed of solid catalyst which is cooled by a cooling medium, wherein said synthesis gas flows, in passing through said catalyst bed, successively through an inflow region for synthesis gas, a hot spot region and an outward gas flow region of temperature substantially declining along an outward gas path therein, said cooling medium being converted into vapor by the transfer of heat arising from methanization and said vapor being superheated in said hot spot region, and wherein:

said cooling medium flows, in countercurrent to said synthesis gas flowing through said catalyst bed, in a cooling medium path which includes one complete transit through said catalyst bed, and the conversion of said cooling medium from a liquid state into vapor is produced by heat transfer both in said outward gas flow region and in said hot spot region.

5. Process according to claim 4, wherein said cooling medium is passed through said outward gas flow region, said hot spot region and said gas inflow region in a first countercurrent pass (15f) through said reactor for vaporization of said cooling medium and is thereafter passed through a portion of said gas flow region adjoining said hot spot region and then through said hot spot region in a second countercurrent pass (16f) for superheating of vapor produced in said first pass (15f).

6. Process according to claim 5, wherein after said first pass (15') of cooling medium through said reactor for vaporization into vapor, the vapor thereby produced is delivered to a vapor chamber (24) from which vapor is led away for the step of passing it, in said second countercurrent pass (16'), for superheating thereof.

* * * * *